US006893473B2

(12) United States Patent
Neogi et al.

(10) Patent No.: US 6,893,473 B2
(45) Date of Patent: May 17, 2005

(54) WHITENED FLUFF PULP

(75) Inventors: Amar N. Neogi, Kenmore, WA (US); Hugh West, Seattle, WA (US); David L. Lee, Tacoma, WA (US)

(73) Assignee: Weyerhaeuser.Company, Federal Way, WA (US)

( * ) Notice: Subject to any disclaimer, the term of this patent is extended or adjusted under 35 U.S.C. 154(b) by 431 days.

(21) Appl. No.: 10/140,679

(22) Filed: May 7, 2002

(65) Prior Publication Data

US 2003/0208859 A1 Nov. 13, 2003

(51) Int. Cl.[7] .......................... D06M 10/00; D21C 9/00
(52) U.S. Cl. ............................. 8/919; 8/115.51; 162/9
(58) Field of Search ................... 8/919, 115.51; 162/9

(56) References Cited

U.S. PATENT DOCUMENTS

| 5,482,514 | A |   | 1/1996  | von Raven |
| 5,536,369 | A | * | 7/1996  | Norlander ................. 162/157.6 |
| 5,766,212 | A |   | 6/1998  | Jitoe et al. |
| 5,834,095 | A | * | 11/1998 | Dutkiewicz et al. ........ 428/191 |
| 5,944,952 | A | * | 8/1999  | Shackford et al. ............ 162/52 |

* cited by examiner

*Primary Examiner*—Hoa Van Le
(74) *Attorney, Agent, or Firm*—Christensen O'Connor Johnson Kindness PLLC

(57) ABSTRACT

Whitened fluff pulp and methods for making whitened fluff pulp. The whitened pulp is a fluff pulp that has been treated with one or more of a white pigment, a colorant, or a fluorescent whitening agent.

22 Claims, 10 Drawing Sheets

Table 1

| Sample ID | Prescriptions | Br | Wh | L* | a* | b* |
|---|---|---|---|---|---|---|
| 82/1 | 82 Brightness Pulp | 81.8 | 66.2 | 96.4 | -0.09 | 5.53 |
| 82/3 | 200 #/ton PCC | 83.5 | 68.9 | 96.1 | -0.20 | 4.73 |
| 82/4 | 200 #/ton+8 oz/ton Blue PTD | 81.0 | 87.3 | 91.4 | 0.23 | -1.70 |
| 82/5 | 4.8 oz/ton Blue RL+2.8 oz/ton BlueRM+30 #/ton ABP-A | 88.5 | 123.9 | 95.4 | 1.26 | -7.84 |
| 82/6* | 200 #/ton PCC+4.8 oz/ton Blue RL+2.8 oz/ton Blue RM+30 #/ton ABP-A | 89.8 | 138.8 | 93.7 | 1.05 | -11.93 |
| 82/7 | 8 oz/ton Blue PTD | 79.1 | 90.6 | 90.3 | -0.14 | -2.91 |
| 82/9 | 200 #/ton PCC + 4 oz/ton Blue PTD | 82.0 | 80.4 | 93.3 | -0.09 | 0.70 |
| 82/10 | 1.2 oz/ton Blue RL+0.7 oz/ton Blue RM +7 #/ton ABP-A | 86.4 | 108.2 | 95.9 | 2.10 | -4.13 |
| 82/11 | 1.2 oz/ton Blue RL+0.7 oz/ton Blue RM +30 #/ton ABP-A | 89.5 | 124.0 | 96.5 | 2.62 | -7.37 |
| 82/12 | 3 oz/ton Blue PTD | 80.0 | 78.1 | 93.1 | -0.30 | 1.09 |
| 82/13 | 200 #/ton PCC+1.4 oz/ton Blue RL+0.8 oz/ton Blue RM +7 #/ton ABP-A | 86.9 | 110.3 | 95.4 | 1.51 | -4.81 |
| 82/14 | 200 #/ton PCC+1.4 oz/ton Blue RL+0.8 oz/ton Blue RM+30 #/ton ABP-A | 90.0 | 126.9 | 95.8 | 2.35 | -8.36 |
| 82/15 | 7 #/ton ABP-A | 86.7 | 106.8 | 96.9 | 2.65 | -3.25 |
| 82/16 | 30 #/ton ABP-A | 90.3 | 121.7 | 97.4 | 3.18 | -6.40 |

FIGURE 3

Table 2

| Sample ID | Prescriptions | Br | Wh | L* | a* | b* |
|---|---|---|---|---|---|---|
| 86/1 | 86 Brightness Pulp | 84.0 | 70.8 | 96.7 | -0.19 | 4.69 |
| 86/3 | 200 #/ton PCC | 86.0 | 74.4 | 96.7 | -0.16 | 3.84 |
| 86/4 | 200 #/ton+4 oz/ton Blue PTD | 82.4 | 85.4 | 93.9 | -0.36 | -0.09 |
| 86/5 | 1.2 oz/ton Blue RL+0.7 oz/ton Blue RM+7 #/ton ABP-A | 89.6 | 122.1 | 96.7 | 1.95 | -6.86 |
| 86/6 | 200 #/ton PCC+2.4 oz/ton Blue RL+1.4 oz/ton Blue RM +7 #/ton ABP-A | 89.2 | 122.9 | 95.3 | 1.23 | -7.69 |
| 86/7 | 2 oz/ton Blue PTD | 80.9 | 78.1 | 94.2 | -.0.57 | 1.69 |
| 86/8 | 200 #/ton PCC+1.4 oz/ton Blue RL+0.8 oz/ton Blue RM +7 #/ton ABP-A | 89.6 | 118.1 | 96.0 | 1.39 | -6.26 |
| 86/9 | 7 lb/ton ABP-A | 89.2 | 114.7 | 97.3 | 2.74 | -4.85 |
| 86/10 | 1 oz/ton Blue PTD | 82.7 | 77.6 | 95.3 | -0.46 | 2.34 |
| 86/11 | 200 #/ton PCC + 1.2 oz/ton Blue PTD | 84.7 | 78.8 | 95.7 | -0.27 | 2.33 |
| 86/12 | 1.2 oz/ton Blue RL+0.7 oz/ton Blue RM + 30 #/ton ABP-A | 90.9 | 128.2 | 97.3 | 2.31 | -7.96 |

FIGURE 5

Table 3

| Sample ID | Prescriptions | Br | Wh | L* | a* | b* |
|---|---|---|---|---|---|---|
| 91/1 | 91 Brightness Pulp | 90.5 | 85.8 | 97.8 | 0.17 | 1.95 |
| 91/3 | 1.2 oz/ton Blue RL+0.7 oz/ton Blue RM +7 #/ton ABP-A | 97.5 | 136.2 | 97.6 | 2.42 | -9.63 |
| 91/4 | 1.2 oz/ton Blue RL+0.7 oz/ton Blue RM +30 #/ton ABP-A | 99.4 | 146.5 | 98.2 | 2.67 | -11.73 |
| 91/5 | 3 oz/ton Blue PTD | 88.6 | 102.6 | 94.6 | 0.29 | -3.49 |
| 91/6 | 1.2 oz/ton Blue RL+0.7 oz/ton Blue RM | 90.2 | 94.3 | 96.6 | -0.80 | -0.64 |
| 91/7 | 7 #/ton ABP-A | 96.5 | 131.6 | 98.7 | 2.89 | -8.03 |
| 91/8 | 30 #/ton ABP-A | 99.2 | 143.0 | 99.0 | 3.36 | -10.55 |
| 91/9 | 0.7 oz/ton Blue RL+1.2 oz/ton Blue RM | 90.5 | 94.3 | 97.0 | -0.26 | -0.40 |

FIGURE 7

Table 4

| Sample ID | Prescriptions | Br | Wh | L* | a* | b* |
|---|---|---|---|---|---|---|
| 70/0 | 77 Brightness CS-10 Pulp | 77.2 | 86.1 | 94.8 | -0.83 | 8.25 |
| 70/1 | 200 #/ton PCC | 73.8 | 79.5 | 93.7 | -0.24 | 9.04 |
| 70/2 | 3 oz/ton Blue PTD | 76.6 | 96.2 | 92.4 | -12.24 | 4.57 |
| 70/4 | 7 lb/ton ABP-A | 78.7 | 102.9 | 95.5 | -0.27 | 4.96 |
| 70/5 | 40 lb/ton ABP-A | 78.1 | 107.5 | 95.7 | -0.08 | 4.08 |
| 70/6 | 200 #/ton PCC + 7 #/ton ABP-A | 77.5 | 117.6 | 95.2 | 0.85 | 1.58 |
| 70/7 | 200 #/ton PCC + 40 #/ton ABP-A | 81.5 | 149.7 | 96.1 | 1.95 | -5.09 |
| 70/8 | 200 #/ton PCC + 1.2 oz/ton Blue RL+0.7 oz/ton Blue RM+7 #/ton ABP-A | 77.7 | 112.1 | 95.3 | 0.18 | 2.84 |
| 70/9 | 200 #/ton PCC + 1.2 oz/ton Blue RL+0.7 oz/ton Blue RM+40 #/ton ABP-A | 79.1 | 134.8 | 95.6 | 0.94 | -2.03 |
| 70/10 | 1.2 oz/ton Blue RL+0.7 oz/ton Blue RM +7 #/ton ABP-A | 79.3 | 107.6 | 95.4 | -0.30 | 3.88 |
| 70/11 | 1.2 oz/ton Blue RL+0.7 oz/ton Blue RM + 40 #/ton ABP-A | 78.2 | 101.6 | 95.0 | -0.42 | 4.96 |

FIGURE 9

WHITENED FLUFF PULP

FIELD OF THE INVENTION

The present invention relates to whitened fluff pulp and methods for making whitened fluff pulp.

BACKGROUND OF THE INVENTION

Bleaching is a common method for increasing the whiteness of pulp. Industry practice for improving appearance of fluff pulp is to bleach the pulp to ever-higher levels of brightness (the Technical Association of the Pulp & Paper Industry ("TAPPI") or the International Organization for Standardization ("ISO")). However, bleaching is expensive, environmentally harsh and often is a source of manufacturing bottleneck. Widespread consumer preference for a brighter, whiter pulp drives manufacturers to pursue ever more aggressive bleaching strategies. While highly bleached pulps are "whiter" than their less-bleached cousins, they are still yellow-white in color. A yellow-white product is undesirable. Countless studies suggest that consumers clearly favor a blue-white over a yellow-white color. The former is perceived to be whiter, i.e., "fresh", "new" and "clean", while the latter is judged to be "old", "faded", and "dirty".

While bleaching directly elevates brightness, it only indirectly elevates whiteness. Due to the latter, bleaching is not always the most efficient method for boosting product whiteness. For example, even after aggressive bleaching, a product's whiteness can always be extended beyond that achievable with bleaching alone by judicious addition of colorant.

The addition of small amounts of blue colorant to improve whiteness appearance is known in other fields, such as papermaking. However, the practice is unknown to the fluff pulp community. The addition of colorant to fluff pulp to improve its whiteness properties is novel to the industry.

The practice of pre-coloring papermaking pulp is not usually done nor is it necessarily desired. With the former, intentional alteration of optical properties often ends up degrading product specifications such as TAPPI brightness, which is undesirable. With the latter, one runs the risk that colorants may not survive the unpredictable manufacturing environments of downstream processes. This is because previously applied colorant can be adversely affected chemically and/or physically during post-processing operations resulting in unexpected or undesirable color changes or even full loss of color. Furthermore, some colorants can be lost or rendered ineffective during various post-processing operations disrupting process health and reliability. Therefore, any optical enhancement is usually accomplished by addition of tinting colorants, fillers, and/or fluorescent dye during the papermaking stage. A process for enhancing the whiteness, brightness, and chromaticity of papermaking fibers has been described in U.S. Pat. No. 5,482,514. The process relates to adding photoactivators, particularly water-soluble phthalocyanines, to papermaking fibers to enhance their optical properties by a catalytic photosensitizer bleaching process. The resulting bleached papermaking fibers can be advantageously incorporated into paper sheets.

With fluff pulp, as well as most pulp and paper products, TAPPI brightness serves as the de facto standard in lieu of an industry-specific whiteness specification such as CIE Whiteness (Commission Internationale d'Eclairage). Because of this, brightness serves two key roles. First, brightness is a manufacturing parameter. Second, brightness is a specification for classifying finished product grades. The implicit, but dubious, assumption to this day has been that brightness is equivalent to whiteness. Common papermaking practice is to either add blue tinting dyes or tinting pigments and/or different types of blue-violet fluorescent dyes to boost whiteness properties. Tinting colorants are either finely ground colored pigments suspended in a dispersant or synthetically produced direct dyes. Tinting dyes have some affinity to cellulose while tinting pigments have little to none. Fluorescent whitening agents (FWA) used in the pulp and paper industry are of three types: di-, tetra-, or hexasulphonated stilbene compounds. These chemicals require ultraviolet (UV) light to excite fluorescence. While there is strong UV content in daylight, even common office lights produce enough UV light to permit some excitation.

Accordingly, there exists a need for pulp having improved whiteness. A need also exists for a method for making whitened pulp. The present invention seeks to fulfill these needs and provides further related advantages.

SUMMARY OF THE INVENTION

In one aspect, the present invention provides whitened fluff pulp. The whitened pulp of the invention is a fluff pulp that has been treated with one or more of a white pigment, a colorant, or a fluorescent whitening agent. In one embodiment, the whitened pulp is a whitened, chemically crosslinked pulp. In another aspect of the invention, airlaid products such as wipes, towels, and tissues, or finished absorbent goods like diapers, feminine hygiene products, or adult incontinent products, can be whitened by either inclusion of the whitened pulp or by whitening of other components, for example, such as the body facing nonwoven, backsheet or superabsorbent polymer (SAP) of a diaper.

In another aspect of the invention, a method for making whitened fluff pulp is provided. In the method, fluff pulp is treated with one or more of a white pigment, a colorant, or a fluorescent whitening agent.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 is a table summarizing the composition and optical properties of representative handsheets including whitened pulp of the invention made from a stock pulp having a brightness of 82;

FIG. 5 is a table summarizing the composition and optical properties of representative handsheets including whitened pulp of the invention made from a stock pulp having a brightness of 86;

FIG. 7 is a table summarizing the composition and optical properties of representative handsheets including whitened pulp of the invention made from a stock pulp having a brightness of 91;

FIG. 9 is a table summarizing the composition and optical properties of representative handsheets including whitened, chemically crosslinked pulp of the invention made from a stock pulp having a brightness of 77.

DETAILED DESCRIPTION OF THE PREFERRED EMBODIMENT

Figure 1:
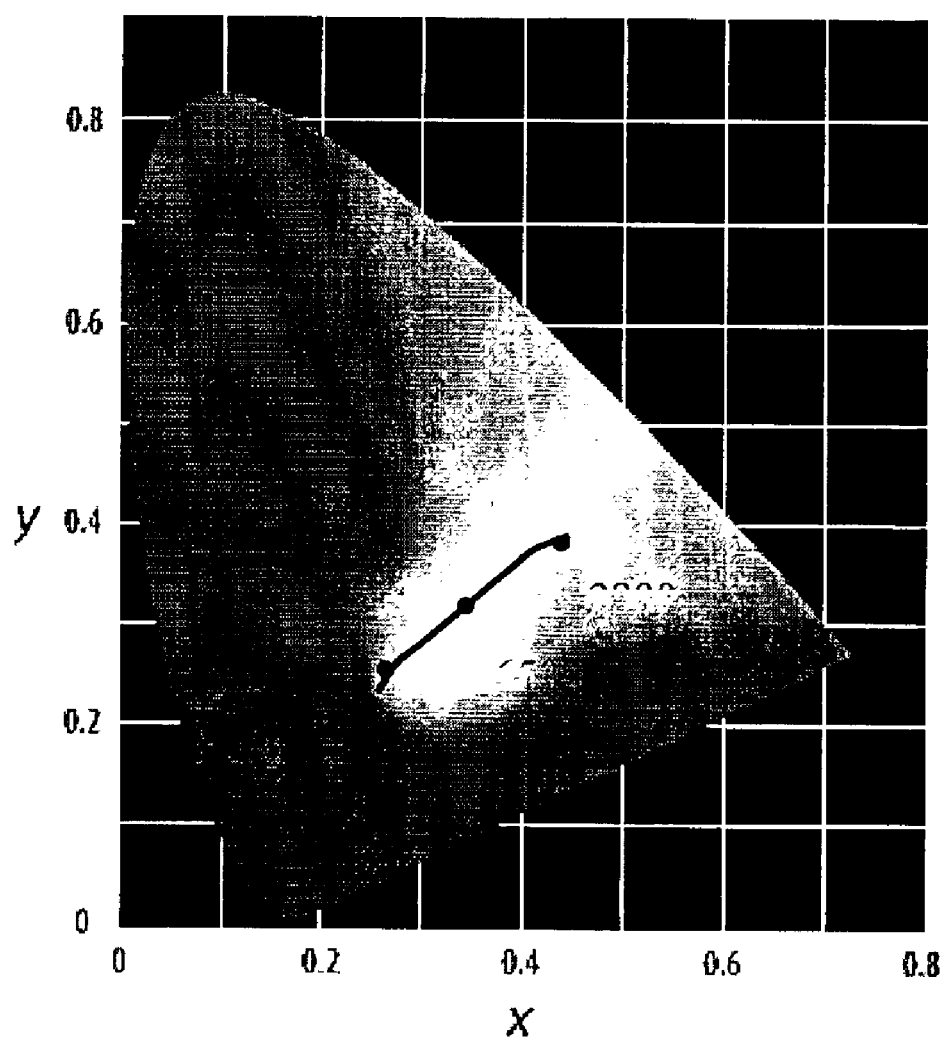
FIG. 1 is a CIE x, y chromaticity diagram.

In one aspect, the present invention provides whitened fluff pulp. The whitened pulp of the invention is a fluff pulp that has been treated with one or more of a white pigment, a colorant, or a fluorescent whitening agent. In another aspect of the invention, a method for making whitened fluff pulp is provided. In the method, fluff pulp is treated with one or more of a white pigment, a colorant, or a fluorescent whitening agent.

The invention provides a method for coloring an unbleached product or lesser-leached product so that it achieves a perceived whiteness comparable to one that has only been more bleached. Coloration, rather than bleaching of fluff pulp, is an alternate and often more efficient whitening strategy. The method of invention provides for ways for coloring low brightness stock so that it achieves higher whiteness. Similarly, the method provides ways for coloring mid- to high-brightness stock so that super-whites can be produced. Furthermore, coloring to the disclosed whiteness target yields an objective parameter that is more closely correlated to subjective whiteness preference than brightness.

In general, the various combinations of colorant amendment strategies achieve a CIE whiteness increase of 60 to 70 points. More specifically, 82 brightness pulp with an initial whiteness of 66, can be elevated to whiteness approaching 140, a 73 point gain. With 86 brightness pulp, whiteness can be boosted from a base whiteness of 71 to 128, a 57 point increase. For a 91 brightness stock, a base whiteness of 86 can be increased to a whiteness of 147, a 61 point gain. With crosslinked pulp having an approximate brightness of 77, it is possible to take initial stock whiteness from 86 to a value of 150, a 64 point increase. Additional increases for all cases are possible with higher dosages of appropriate white filler and/or fluorescent dye.

Fluff pulp suitable for whitening in accordance with the present invention can include any fluff pulp that is receptive to receiving and retaining one or more of the whitening materials useful in improving the whiteness of fluff pulp. Suitable fluff pulp includes traditional fluff pulp, chemically crosslinked fluff pulp, and superabsorbent fluff pulp, among others. Representative examples of superabsorbent fluff pulp are described in WO 01/529911, Superabsorbent Cellulosic Fiber, and U.S. application Ser. No. 09/939,182, Superabsorbent Polymer, each incorporated herein by reference in its entirety. Bleached and unbleached fluff pulp can be whitened in accordance with the method of the invention. Also, commonly used superabsorbent polymers contained within the absorbent product can be whitened by this method. Examples of such super absorbent polymers are derived from acrylic acid and manufactured by companies such as Dow Chemical or Nippon Shokubai.

The whitened fluff pulp of the invention can be prepared by treating fluff pulp with one or more whitening materials. As noted above, suitable whitening materials include white pigments, colorants, and fluorescent whitening agents. The whitened fluff pulp of the invention can include one whitening material, or a combination or two or more of these materials. The choice of whitening material(s) in a particular fluff pulp will depend on the desired whiteness of the pulp product, the nature and use of the whitened pulp-containing product, and any applicable cost constraints.

The whitened fluff pulp of the invention can include one or more white pigments. Suitable white pigments include any pigment or mixture of pigments having reflectance spectra greater than or similar to the stock fluff pulp from which the whitened fluff pulp is made. Suitable white pigments also effectively substitute for fiber in the whitened pulp and ultimately in the end pulp product. Accordingly, the amount of white pigment added to the stock fluff pulp will depend on the nature of the end product. Because the white pigment is a fiber substitute, the amount of white pigment added to the pulp will depend on the whitened pulp's desired whiteness and strength. The greater the amount of white pigment added, the greater the whiteness of the pulp and the lower the tensile strength of the pulp and products incorporating the pulp. The amount of white pigment that is added to the pulp will be limited by the amount of the pigment that can be retained by the pulp. In addition to improved whiteness and because white pigment is less expensive than fiber, there is also an economic advantage associated with substituting pigment for fiber in the pulp and pulp products. Representative white pigments (or fillers) include precipitated calcium carbonate (PCC), titanium dioxide, barium sulfate, aluminum trihydrate, talc, zinc sulfide, diatomaceous silica, clay, blanc fixe, synthetic organic and inorganic pigments, and high brightness chalk, among others. The pigment is added to the pulp in an amount from about 50 to about 400 pounds per ton fiber. In one embodiment, the whitened fluff pulp includes precipitated calcium carbonate. In one embodiment, the precipitated calcium carbonate is present in the pulp in an amount of about 200 pounds per ton fiber. As noted above, the whitened pulp can include one or more fluorescent whitening agents and/or one or more colorants in combination with the white pigment.

The whitened fluff pulp of the invention can include one or more fluorescent whitening agents (FWA). Fluorescent whitening agents are known and commercially available from a variety of sources. Fluorescent whitening agents are commonly referred to as optical brighteners and depending on type, upon excitation, either emit blue-violet, blue, or green-blue light. Fluorescent whitening agents are generally anionic. Suitable fluorescent whitening agents are fluorescent dyes including, for example, sulfonated stilbene compounds. Representative sulfonated stilbene compounds include di-, tetra-, and hexasulfonated stilbene products. In one embodiment, the whitened fluff pulp includes a tetrasulfonated stilbene compound commercially available under the designation Tinopal ABP-A from Ciba Specialty Chemicals, High Point, N.C.; Leucophor family of products from Clariant Corporation, Charlotte, N.C.; Blankophor ER products from Bayer AG, Pittsburgh, Pa. The fluorescent whitening agent is added to the pulp in various ways using an amount from about 1 to about 40 pounds or more per ton fiber depending on compound type and concentration. In one embodiment, the whitened fluff pulp includes a tetrasulfonated stilbene compound. In one embodiment, the tetrasulfonated stilbene compound is present in the pulp in an amount of about 40 pounds per ton fiber. In another embodiment, the tetrasulfonated stilbene compound is present in the pulp in an amount of about 30 pounds per ton fiber. In another embodiment, the tetrasulfonated stilbene compound is present in the pulp in an amount of about 7 pounds per ton fiber. As noted above, the whitened pulp can include one or more white pigments and/or one or more colorants in combination with the fluorescent whitening agent.

The whitened fluff pulp of the invention can include one or more colorants. As used herein, the term "colorant" refers to tinting dyes and tinting pigments. Unlike pigments, which are typically mechanically retained within fluff pulp, dyes react and bond to the fibers of the fluff pulp. Suitable colorants are known and commercially available from a variety of sources. Suitable colorants include blue pigments and dyes. Representative blue colorants are commercially available from Ciba Specialty Chemicals, High Point, N.C., under the designations Irgalite Blue RL, Irgalite Blue RM and Pergasol Blue PTD (formerly Pergasol Blue BVC), Levacel products from Bayer AG, and Cartasol products from Clariant. The colorant is added to the pulp in an amount from about 1 to about 25 ounces per ton fiber depending on colorant concentration. In one embodiment, the whitened fluff pulp includes a blue dye. In one embodiment, the blue dye is present in the pulp in an amount of about 3 ounces per ton fiber. As noted above, the whitened pulp can include one or more white pigments and/or one or more fluorescent whitening agent in combination with the colorant.

In one embodiment, the whitened pulp includes tinting dye, precipitated calcium carbonate, and a fluorescent whitening agent. In one embodiment, the whitened pulp includes two tinting dyes, 200 pound per ton precipitated calcium carbonate, and 30 pounds per ton of fluorescent whitening agent. This embodiment has a whiteness of 127. In another embodiment, the whitened pulp includes two tinting dyes, 200 pounds per ton precipitated calcium carbonate, and 7 pounds per ton of fluorescent whitening agent. This embodiment has a whiteness of 127.

In one embodiment, the whitened pulp includes a colorant only. In this embodiment, the colorant is a blue tinting dye present in about 3 ounces per ton fiber.

In another embodiment, the whitened pulp includes 3 ounces per ton blue tinting dye, 200 pound per ton precipitated calcium carbonate, and 40 pounds per ton of a fluorescent whitening agent. This embodiment has a whiteness of 160.

Representative whitened pulps and handsheets including the pulps are described in Examples 2–5.

To further illustrate the principles of the invention, a discussion of whiteness and brightness is useful. Webster's Dictionary defines white as "the object color of greatest lightness characteristically perceived to belong to objects that reflect diffusely nearly all incident energy throughout the visible spectrum". Used as a noun or adjective, white is defined as "free from color". Most natural and many man-made products are never "free from color". Whether the "white" product is fluff pulp, paper, textiles, plastics, or teeth, there is almost always an intrinsic color other than white, associated with it. Consider two hypothetical objects, the first which meets Webster's definition of white, i.e., one characterized by a flat spectrum of high reflectance and a second, which is the first with a small amount of blue colorant added (results in an unequal spectrum). Most people will judge the second as being the whiter of the two even though its total reflectance is lower in certain spectral regions. The first will be judged as a "yellow-white" while the second a "blue-white". Human color vision is more than just a sensation. It is also quite subjective and certain associations are unconsciously made. This is why the blue-white object is associated with "clean and pure" while the "yellow-white" is "dirty, old or impure". Exactly what type of fillers, colorants and which hues to use (red-blue, green-blue, etc.), how much to apply and the optical prescription to target has been the subject of considerable interest.

As noted above, bleaching is expensive, environmentally harsh and often is a source of manufacturing bottleneck. While bleaching directly elevates brightness, it only indirectly elevates whiteness. Due to the latter, bleaching is not always the most efficient method for boosting product whiteness. For example, even after aggressive bleaching, a product's whiteness can always be extended beyond that achievable with bleaching alone by judicious addition of colorant. Furthermore, it is possible to color an unbleached product so that it achieves a perceived whiteness comparable to one that has only been bleached. Coloration, rather than bleaching of fluff pulp, is an alternate and often more efficient whitening strategy. The method of invention provides for ways for coloring low brightness (and low whiteness) stock so that it achieves higher whiteness. Similarly, it provides ways for coloring mid to high-brightness (mid to high whiteness) stock so that super-whites can be produced. Furthermore, coloring to the desired whiteness target yields an objective parameter that is more closely correlated to subjective whiteness preference than brightness.

The color science behind the method of invention are predicated on four concepts: (a) human preference for whiteness over brightness, (b) chromatic adaptation, (c) white point invariance to illuminant and (d) white point prescription model.

Whiteness attribute, not TAPPI brightness, better correlates with customer preference for product whiteness. When people are given a choice between two products having equal TAPPI brightness, usually the product exhibiting the higher whiteness attribute is preferred. The application of CIE Whiteness is but one measure of such a whiteness attribute. Similarly, a product having higher whiteness than the product to which it is being compared is preferred even when the former exhibits a lower brightness. TAPPI Brightness in North America and ISO Brightness throughout the rest of the world, are pulp and paper industry-specific standards used to loosely quantify the "whiteness" of product. Regardless of which standard is applied, TAPPI or ISO, brightness is defined as the percent reflectance of product measured at an effective wavelength of 457 nm. In general, higher brightness is perceived by the industry to imply higher whiteness, but this is not always the case. Because brightness is a band-limited measurement taken in the blue end of the visible spectrum, it essentially measures how blue a product is. If one relies solely on a brightness specification, it is possible to maximize TAPPI brightness, yet produce a product that appears blue, not white. Brightness provides little indication as to how white a product is nor does it tell us anything about its lightness, hue, or saturation. As a whiteness specification, it is insufficient. Such is the danger of pursuing brightness when whiteness is the principal objective.

The perceived color of an object depends on the spectral characteristics of the light source used to view it. Light sources found in the typical home are incandescent having a correlated color temperature (CCT) of 2800° Kelvin while those in the office are various types of fluorescent lights, varying between warm-white (3000° K), cool white (4000°

K) and daylight (6500° K). A remarkable characteristic of the human visual system is its ability to readily adapt to a new white point when the color of ambient light changes. For example, white paper will continue to "look white" when viewed under an incandescent bulb (rich in red light) or under daylight (rich in blue light). Adaptation is the physiological term used to describe the process by which the human visual system changes its sensitivity, depending on the luminances prevailing in the visual field. For example, the system adjusts to processing lower light levels even though it was exposed to a high light level environment before. While there are several types of receptive cells in the eye, sensitive to different wavelengths of the visible spectrum, chromatic adaptation is the mechanism which manages the "white balance" or white point reference of the eye. If the new lighting situation has a different correlated color temperature, for example, there is an increased amount of red light relative to the total amount of light (incandescent source), then the cells responsible for sensing red light will reduce their sensitivity relative to the sensitivity of the other cells. As a result, a white surface will again appear white to the observer after a certain time and not pink, despite the object reflecting a dis-proportionally greater amount of red light.

In practical terms, the above leads one to conclude that the human visual system's determination of "white point" with non-fluorescing objects is essentially invariant to the color of the illuminant. This ability is a key survival mechanism and an important gift of nature. If the color of objects (all colors including white) depended on the color of the illuminant, there would be serious problems recognizing dangerous situations and threatening environments. Furthermore, for two, non-fluorescing "white" objects, if one appears whiter than the other under a given light source, the above phenomenon leads one to conclude that it will continue to look whiter in other light sources despite the spectral differences, however large or small, in illuminant composition, provided the source is polychromatic.

The term "white point prescription model" refers to quantification of whiteness, i.e., a method for mathematically defining a practical whiteness parameter. Human color vision is three-dimensional, i.e., photoreceptors in the eye are sensitive to three broad regions in the visible spectrum, red, green, and blue. Post-processing of the visual stimuli within the brain gives rise to the ultimate sensation of color. Vision models for quantifying color require three parameters: either three tri-stimulus values (X, Y, Z) or some metric which provides for a hue, saturation and lightness component. The tri-stimulus values represent the amount of light sensed in three narrow band channels, red (X), green (Y) and blue (Z). The color coordinates of all colors can be plotted in a chromaticity diagram (CIE), which expresses each color based on its chromaticity coordinates. Chromaticity values are calculated by normalizing the tri-stimulus values ($x=X/[X+Y+Z]$, $y=Y/[X+Y+Z]$, $z=Z/[X+Y+Z]$). A white object possesses chromaticity coordinates x, y, and z in the vicinity of ⅓. FIG. 1 is a plot of the CIE chromaticity diagram. The locus of white points defines the chromaticities of a black body (Planckian) radiating at different temperatures. Referring to FIG. 1, the horseshoe-shaped region is boundary of visible colors; the x and y axes represent the relative amounts of each of the red and green primaries, respectively; equal values (0.33, 0.33, 0.33) theoretically yields an equal-energy white; the white point locus (black curve) describes the chromaticity coordinates of a black body radiating at various temperatures; moving from 2800° K to 12,000° K, the black body appears yellow-white, then neutral, and eventually to blue-white in color.

The present invention provides a model-based method for specifying product whiteness; a method for selecting colorants optimal to the whitening task; application of the model-based method for establishing a family of parametric whiteness targets; methods for defining acceptance zones for product whiteness encompassing the targets; and a robust coloring method that yields product white points that are perceived to be invariant to light source.

Representative whitened pulps of the invention and methods for making the pulps are described in Examples 2–5. In these examples, three "regular" pulps, a southern pine and two northern softwood pulps were cooked to three brightness levels, 82, 86 and 91. A chemically crosslinked pulp (a citric acid crosslinked pulp) was the fourth pulp and had a brightness of 77, noticeably yellower in shade than the first three. These four "undoped" (i.e. uncolored) pulps are referred to as Control 82, Control 86, Control 91 and Control 70, respectively. Examples 1 and 2 describes the feasibility of doping Control 82 and Control 86 with colorants to determine if the colored pulps can meet or exceed the whiteness of Control 91. Example 3 applies prescriptions (i.e., the whitening materials and methods) from Examples 1 and 2 to Control 91 to produce a "super white" pulp. Example 4 describes ways to increase the whiteness of Control 70 pulp.

Starting with an 82 brightness pulp, the majority of the prescriptions demonstrate an improvement in whiteness. In Example 2, modest amounts of two blue tinting pigments combined with 200 lb/ton precipitated calcium carbonate (PCC) and 30 lb/ton of fluorescent whitening agent (FWA) produced a colored pulp that meets the brightness of Control 91, yet achieves a whiteness of 127, which is over 41 points higher than the whiteness of Control 91. In Example 3, modest amounts of two blue tinting pigments combined with 200 lb/ton PCC and 7 lb/ton of FWA produced a colored pulp that approximately meets the brightness of Control 91, yet achieves a whiteness of 123, which is over 37 points higher than the whiteness of Control 91. Example 4 provides results for pulp handsheets. In Example 4, a prescription including 200 lb/ton PCC and pigment blue combined with 30 lb/ton of FWA yields a colored pulp that achieves a brightness in excess of 100 and an estimated whiteness above 150. In Example 5, a 3 ounce/ton addition of blue dye reduces brightness about 1 point, yet elevates whiteness from 86 to 96 points. This is the simplest of all prescriptions, yet it produces a considerable improvement in whiteness. If filler and FWA addition are not an issue, an even better prescription includes 200 lb/ton PCC, 3 ounce/ton of blue dye, and 40 lb/ton FWA. This formulation produces a colored pulp that achieves an estimated brightness of 82 and a whiteness of about 160.

The examples demonstrate that the "dyeing" of pulp with fillers, colorants, and FWAs is a viable approach for improving its whiteness. In the examples, various colorant strategies are described and are referred to as "filler-only", "dye or pigment-only", "FWA-only", and "combined".

Figure 2:
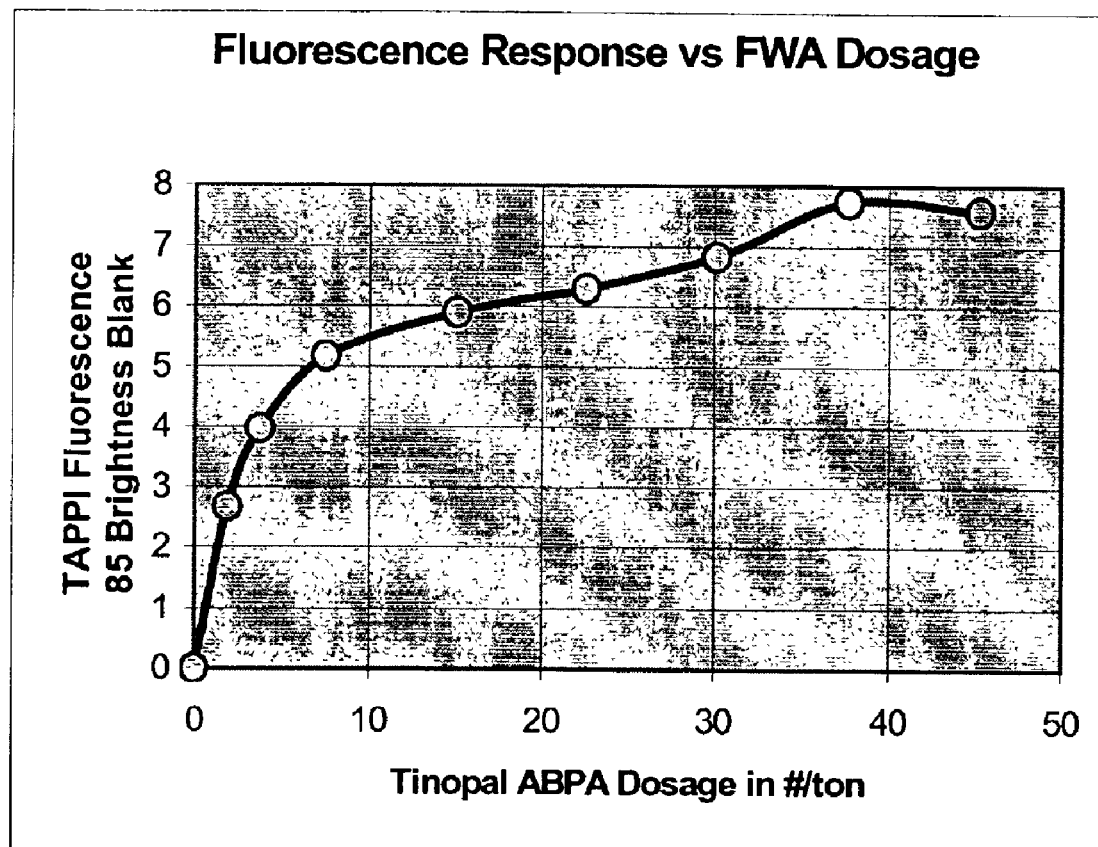
FIG. 2 is a graph illustrating TAPPI fluorescence response as a function of dosage for a representative tetrasulfonated stilbene compound useful as a fluorescent whitening agent in the present invention.

Ciba's ABP-A response curve on generic pulp is given in FIG. 2. Two Ciba pigment blue dyes (Irgalite Blue RL and Irgalite Blue RM) and one direct blue dye (Pergasol Blue PTD, formerly Pergasol Blue BVC) were also used as whitening materials. Irgalite Violet B was considered, but not used because its tinting characteristics made handsheets appear too red for the required level of blueness needed to achieve a neutral white point.

The whitened pulp of the invention can be advantageously incorporated into a variety of products including, for example, airlaid products, such as tissue, toweling, and wipes; and personal care absorbent products, such as infant diapers, incontinence products, and feminine care products.

The whitened pulp of the invention can be incorporated into a diaper. A diaper typically includes an absorbent core surrounded by nonwoven facing and backing sheets. The absorbent core includes fluff pulp fibers and superabsorbent material. A diaper's core can include the whitened fluff pulp fibers of the invention. The diaper can also include a whitened facing and/or backing sheet. The facing and backing sheets can be made from the whitened fibers of the invention, or alternatively, whitened by the methods of the invention. The method for whitening fluff pulp fibers described herein is also applicable to whitening superabsorbent materials, including superabsorbent cellulosic materials and superabsorbent synthetic materials (e.g., superabsorbent polymers, SAP, such as polyacrylates). Accordingly, the diaper can also include whitened superabsorbent material.

The following examples are provided for the purposes of illustrating, not limiting, the invention.

EXAMPLES

Example 1
The Preparation of Handsheets Including Whitened Pulp

In this example, the preparation of handsheets that include whitened pulp is described. The characteristics of the whitening materials are provided.

Handsheets/pads were made in the following manner. Four gram handsheets were made from the "regular" pulps (82, 96, 91 brightness) and 12 gram pads were made from the crosslinked pulp (citric acid crosslinked pulp). The amounts and order of chemical addition was as follows:

(1) Pulp;
(2) De-ionized water, 90 mls;
(3) Water hardness, 10 mls (takes water hardness to 100 ppm);
(4) PCC, 200 lbs./ton (10% nominal filler loading);
(5) Dye/pigment/FWA;
(6) Alum (for tinting pigment only), 10 lbs./ton; and
(7) Retention aid (in the sheet mold), 0.5 lbs./ton.

For the crosslinked pulp pad, the crosslinked pulp was added to blender before PCC.

The PCC was Albacar HO (specification states dry brightness of 97).

While handsheets were made using traditional methods, the crosslinked pulp pads were made under different conditions in an effort to produce better formation and improve retention. For these pads, the crosslinked pulp slurry was mixed in a blender at its lowest speed for about 2 minutes and then added to the sheet mold. Within the sheet mold, a 5" diameter cup was inserted to serve as a circular template. For a given grammage, a small, circular area improved pad formation over a large, rectangular shape. Two sheets (top/bottom) of aluminum foil were used to sandwich the pad and then additional sheets of blotter paper added on both sides to minimize loss of additives when water drained during the pressing operation. Foil was used because excessive amounts of FWA were being wicked by the paper blotters.

Material Characteristics

Pergasol Blue PTD liquid is an anionic direct dye having good affinity to cellulose. Irgalite Blue RL Paste and Irgalite Blue RM Paste are highly concentrated pigments delivered in paste form. Pigments in general are nonionic. However, the dispersants used are anionic, therefore overall, they are slightly anionic. With little affinity to fiber, the pigments rely on mechanical entrainment for their tinting properties.

In general the majority of FWAs used in papermaking are anionic. There are some, not many, cationic ones but they are for specialized use, i.e., if used in paper they are primarily for ink jet applications, otherwise they are common in the textile industry. Of the three types of anionic FWAs, the disulfonated stilbene compound has the least anionic charge whereas the difference between the tetrasulfonated and hexasulfonated stilbene compounds is small with the hexasulfonated line being slightly more anionic. Tinopal ABP-A is a tetrasulfonated stilbene compound.

Whiteness Results.

All visual evaluations, while subjective, were made under various illuminants (CIE Illuminant D65, Incandescent, Cool White Fluorescence (CWF), Horizon) using a Macbeth SpectraLight II viewing booth and a neutral grey surround. Informal assessment under office lighting with a correlated color temperature about 3000° K supported the viewing booth conclusions (i.e. the human visual system's unique ability to adapt, the phenomenon of chromatic adaptation, to different-colored light sources is the reason behind why the judgment of "white" seems so remarkably invariant to type of viewing source.

Example 2
The Preparation of Handsheets Including Whitened Pulp: Stock Pulp Brightness 82

Figure 4:
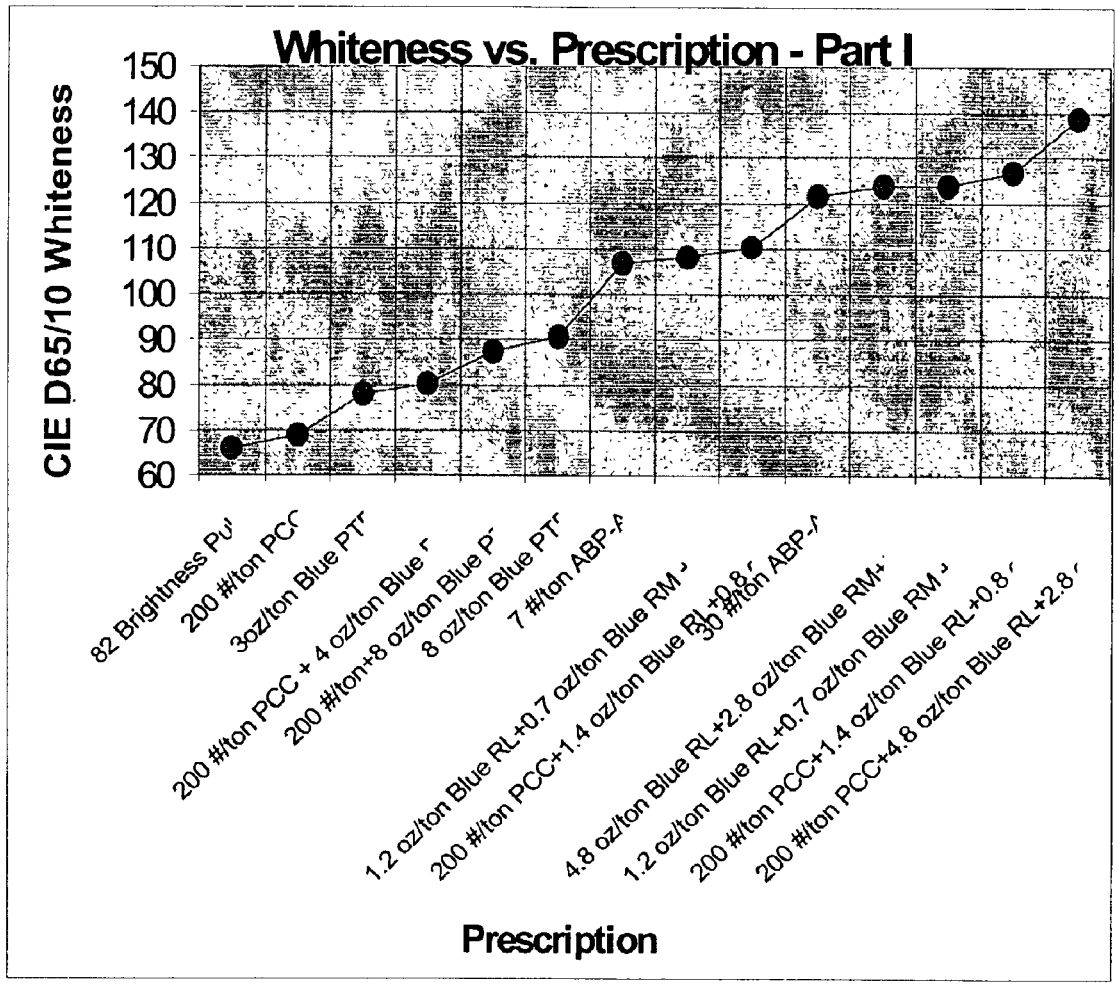
FIG. 4 is a graph of whiteness as a function of prescription for representative handsheets including whitened pulp of the invention made from a stock pulp having a brightness of 82.

In this example, the preparation of handsheets that include whitened pulp is described. The stock pulp for these handsheets was fluff pulp having a brightness of 82 (Control 82). The prescriptions (i.e., whitening materials and methods) are designated as "filler-only", "blue-dye-only", "FWA-only", and "combined". The optical results (e.g., brightness and whiteness) for representative handsheets including whitened pulp are summarized in Table 1 in FIG. 3. Regarding Table 1, TAPPI Method 452 Brightness (Br) was measured on a Technidyne S4 Brightimeter; CIE Whiteness (Wh) and CIELAB D65/10 (CIE Illuminant D65 and 10 Degree Standard Observer) L*a*b* parameters were measured with a DataColor Spectraflash 500. TAPPI Brightness and CIE Whiteness include fluorescence components, if present, based on an ultra-violet content level equivalent to that typically generated by a quartz-tungsten-halogen light source. A graph of whiteness as a function of prescription for representative handsheets including whitened pulp is provided in FIG. 4.

Filler-only

A 10% PCC loading (Sample 82/3) boosts brightness by 1.5 to 2.0 points and whiteness by about 3 points with respect to Control 82. The whiteness preference of Sample 82/3 over Control 82 is noticeable.

Blue Dye-only

A 3 ounce/ton addition of blue PTD dye (Sample 82/12) reduces brightness roughly 1 point but elevates whiteness by 12 points from 66 to 78. The whiteness preference for Sample 82/12 over Control 82 is considerable. While this sheet is still somewhat yellower than Control 91 (Brightness 91, Whiteness 86), the visual differences between Control 82 and Control 91 are even greater.

FWA-only

A 7 lb/ton addition of FWA (Sample 82/15) boosts brightness by 5 points as expected, but elevates whiteness by about 40 points relative to Control 82. If dosage is increased to 30 lb/ton (Sample 82/16n), then a final brightness of about 90 is achieved with a corresponding whiteness of 122. Both appear whiter than Control 91.

Combined

Best opticals are obtained with Sample 82/14. Modest amounts of two tinting pigments (Blue RL and Blue RM)

combined with PCC (10% loading) and 30 lb/ton of FWA produce a colored pulp that meets the brightness of Control 91 yet achieves a whiteness of 127 which is over 41 points higher than the whiteness of Control 91. Sample 82/13 is advantageous as neither whiteness (110) nor brightness (87) is compromised drastically.

Note that dosages of tinting dye and FWA can be increased slightly to compensate for the higher surface area contributed by the filler. Colorant dosages will be increased slightly.

Conclusions

Modest amounts of two tinting pigments, 200 lb/ton PCC and 30 lb/ton of FWA applied to Control 82 produce a colored pulp that meets the brightness of Control 91, yet achieves a whiteness of 127, which is over 41 points higher than the whiteness of Control 91.

Example 3

The Preparation of Handsheets Including Whitened Pulp: Stock Pulp Brightness 86

Figure 6:
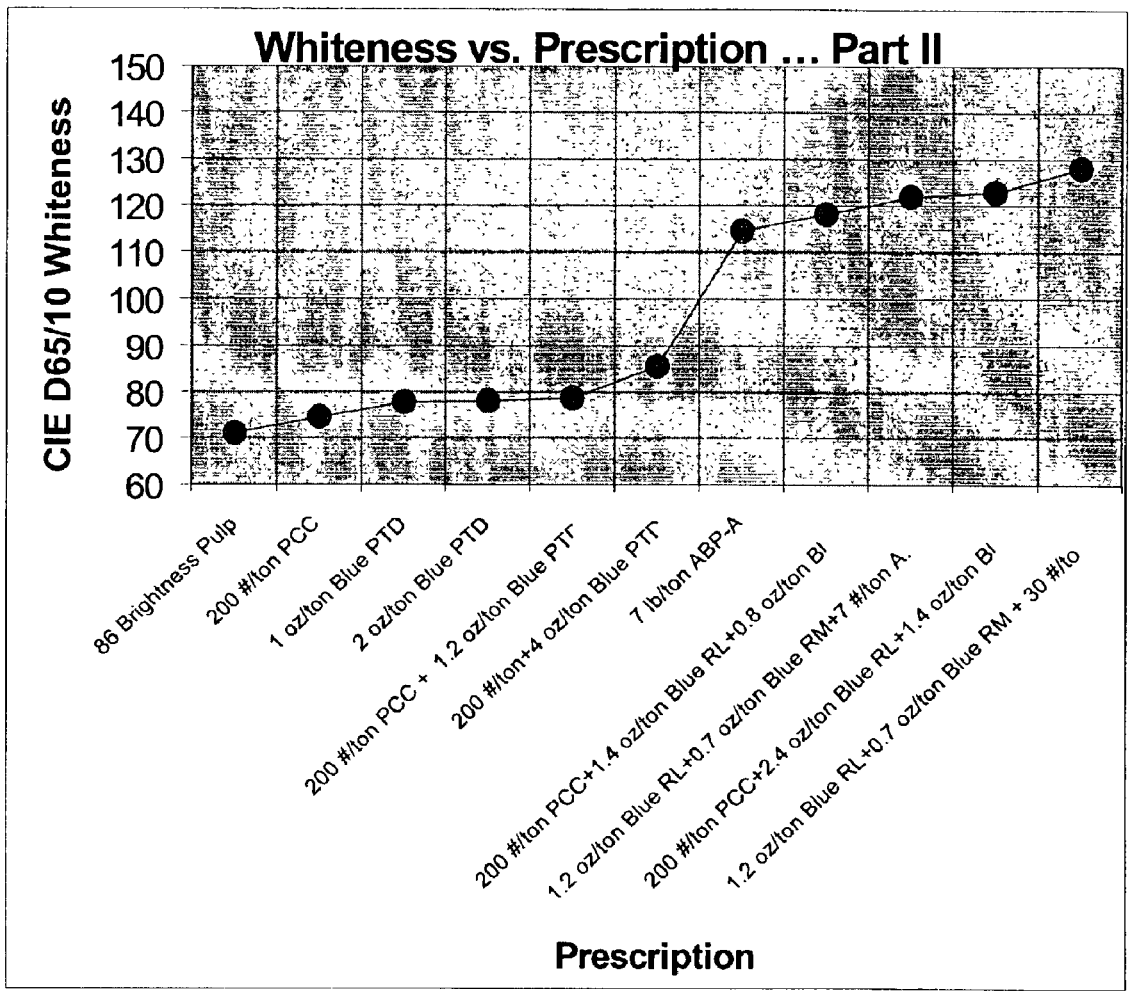
FIG. 6 is a graph of whiteness as a function of prescription for representative handsheets including whitened pulp of the invention made from a stock pulp having a brightness of 86.

In this example, the preparation of handsheets that include whitened pulp is described. The stock pulp for these handsheets was fluff pulp having a brightness of 86 (Control 86). The prescriptions (i.e., whitening materials and methods) are designated as "filler-only", "blue-dye-only", "FWA-only", and "combined". The optical results (e.g., brightness and whiteness) for representative handsheets including whitened pulp are summarized in Table 2 in FIG. 5. Regarding Table 2, TAPPI Method 452 Brightness (Br) was measured on a Technidyne S4 Brightimeter; CIE Whiteness (Wh) and CIELAB D65/10 L*a*b* parameters were measured with a DataColor Spectraflash 500. TAPPI Brightness and CIE Whiteness include fluorescence components, if present, based on an ultra-violet content level equivalent to that typically generated by a quartz-tungsten-halogen light source. A graph of whiteness as a function of prescription for representative handsheets including whitened pulp is provided in FIG. 6.

Filler-only

A PCC loading of 10% (Sample 86/3) boosts brightness by about 2 points and whiteness by 3 points with respect to Control 86. There is a noticeable difference in appearance with 86/3 being preferred to Control 86.

Blue dye-only. A 2 oz/ton addition of blue dye (Sample 86/7) reduces brightness roughly 2 points but elevates whiteness by 7 points from 71 to 78. Once again, sheet 86/7's whiteness is preferred to Control 86. While this sheet is still somewhat yellower than Control 91 (Brightness 91, Whiteness 86), the visual differences between Control 86 and Control 91 are even greater.

FWA-only. A 7 lb/ton addition of FWA (Sample 86/9) boosts brightness by 5 points but elevates whiteness by about 44 points to 115, relative to Control 86. This sample is a good whiteness match to Control 91 even though brightness is only about 89. If desired, one can easily exceed control by increasing the FWA dosage to 30 lb/ton.

Combined

Best opticals are obtained with Sample 86/6. Modest amounts of two tinting pigments (Blue RL and RM) combined with PCC (10% loading) and 7 lb/ton of FWA produce a colored pulp that approximately meets the brightness of Control 91 yet achieves a whiteness of 123, which is over 37 points higher than the whiteness of Control 91. If higher brightness is required, it would be advantageous to fill with a loading of 10% PCC to the above prescription. The prescription would yield an estimated brightness of 92 and whiteness of 132.

Conclusions

Modest amounts of two blue tinting pigments combined with 200 lb/ton PCC and 71 lb/ton of FWA added to Control 86 produce a colored pulp that approximately meets the brightness of Control 91, yet achieves a whiteness of 123, which is over 37 points higher than the whiteness of Control 91.

Example 4

The Preparation of Handsheets Including Whitened Pulp: Stock Pulp Brightness 91

Figure 8:
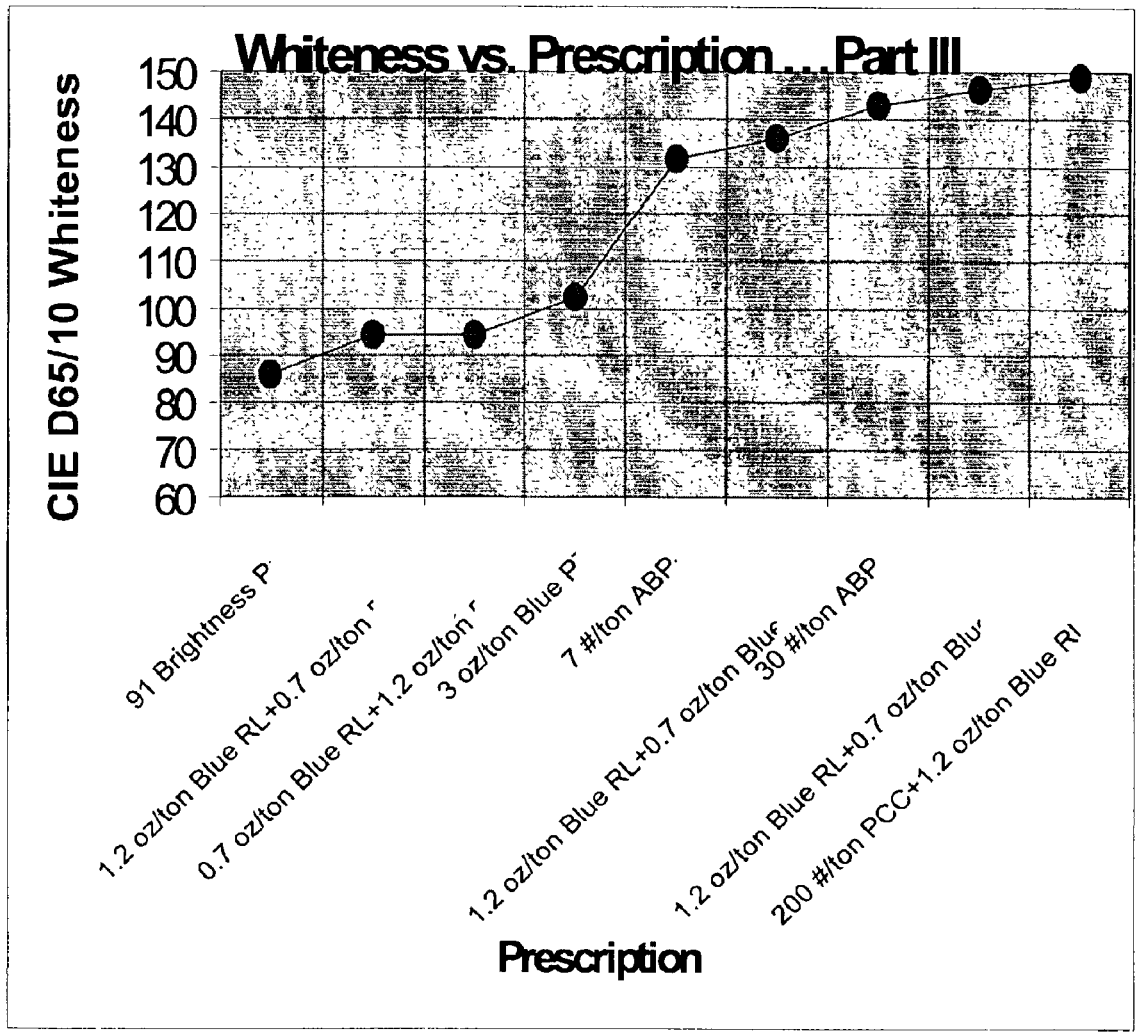
FIG. 8 is a graph of whiteness as a function of prescription for representative handsheets including whitened pulp of the invention made from a stock pulp having a brightness of 91.

In this example, the preparation of handsheets that include whitened pulp is described. The stock pulp for these handsheets was fluff pulp having a brightness of 91 (Control 91). The prescriptions (i.e., whitening materials and methods) are designated as "filler-only", "blue-dye-only", "FWA-only", and "combined". The optical results (e.g., brightness and whiteness) for representative handsheets including whitened pulp are summarized in Table 3 in FIG. 7. Regarding Table 3, TAPPI Method 452 Brightness (Br) was measured on a Technidyne S4 Brightimeter; CIE Whiteness (Wh) and CIELAB D65/10 L*a*b* parameters were measured with a DataColor Spectraflash 500. TAPPI Brightness and CIE Whiteness include fluorescence components, if present, based on an ultra-violet content level equivalent to that typically generated by a quartz-tungsten-halogen light source. A graph of whiteness as a function of prescription for representative handsheets including whitened pulp is provided in FIG. 8.

Filler-only

While no filled handsheets were made, it can be inferred from Examples 2 and 3 that a PCC loading of 10% will boost brightness by about 2 points and whiteness by 3–4 points with respect to Control 91.

Blue Dye-only

A 3 ounce/ton addition of blue dye PTD (Sample 91/5) reduces brightness roughly 2 points, but elevates whiteness by 17 points from 86 to 103. While this sheet is technically lower in brightness, it is considerably whiter than Control 91 in appearance (Brightness 91, Whiteness 86). This sample is a good white relative to Control 91.

FWA-only

A 7 lb/ton addition of FWA (Sample 91/7) boosts brightness by 6 points but elevates whiteness by about 46 points to 132, relative to Control 91. This sample is a visibly superior white relative to Control 91.

FWA-Blue Dye

Sample 91/4 consists of two blue tinting pigments and 30 lb/ton FWA. This sheet achieves a whiteness index of 147 and a brightness of 99, which is the highest of the representative samples. This sheet is also visually the whitest sheet in the set.

Combined

Based on prescriptions of Examples 2 and 3, a prescription for 91 brightness pulp includes filler addition to further boost the white point and reduce fiber loading. A formulation of 200 lb/ton PCC, Pigment Blue RL and RM combined with 30 lb/ton of FWA yields a colored pulp that achieves a brightness in excess of 100 and a projected whiteness above 150.

Conclusions

A prescription consisting of 200 lb/ton PCC, pigment blue dye and 30 lb/ton of FWA should boost Control 91's brightness to about 100 and a whiteness above 150.

Example 5
The Preparation of Handsheets Including Whitened Pulp: Stock Pulp Brightness 77

Figure 10:
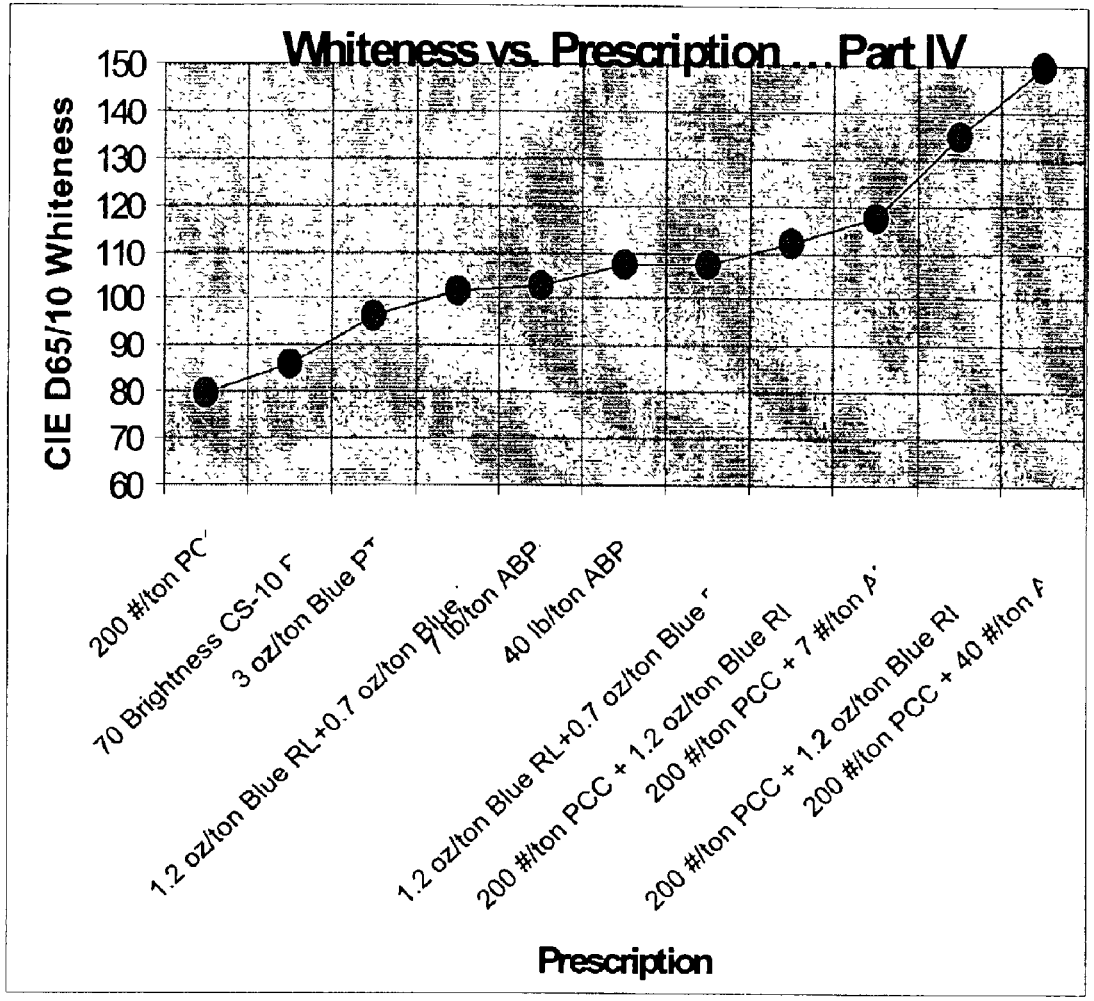
FIG. 10 is a graph of whiteness as a function of prescription for representative handsheets including whitened pulp of the invention made from a stock pulp having a brightness of 77.

In this example, the preparation of handsheets that include whitened pulp is described. The stock pulp for these handsheets was chemically crosslinked pulp (citric acid crosslinked pulp) having a brightness of 77 (Control 70). The prescriptions (i.e., whitening materials and methods) are designated as "filler-only", "blue-dye-only", "FWA-only", and "combined". The optical results (e.g., brightness and whiteness) for representative handsheets including whitened pulp are summarized in Table 4 in FIG. 9. Regarding Table 4, ISO Method 2470 Brightness (Br), CIE Whiteness (Wh), and CIELAB D65/10 L*a*b* parameters were measured with a Minolta CM3700d spectrophotometer. ISO Brightness was approximated by the Minolta meter. Brightness and Whiteness include fluorescence components, if present, based on an ultra-violet content level equivalent to that typically generated by a quartz-tungsten-halogen light source. All measurements are a mean of four readings acquired through a 12" diameter aperture using integrating sphere geometry. A graph of whiteness as a function of prescription for representative handsheets including whitened pulp is provided in FIG. 10.

In this example the data is more variable due to pad-making and measurement difficulties. In general, addition of filler and FWA is beneficial. Furthermore, on chemically crosslinked pulp, blue PTD dye performs better than the blue pigments. Spectral curves show little indication of any blue "signature" in those pads presumed to contain pigment blue. Prescriptions based on addition of all three produce a colored pulp with a 5 point gain in brightness and over 60 point gain in whiteness.

The optical role of filler is quite different when used with chemically crosslinked pulp. With regular pulps, FWA dyes both fiber and filler in a predictable manner. For a fixed level of FWA, addition of filler actually reduces fluorescence slightly compared to a sheet containing FWA only. This is because some of the FWA is "buried" within the sheet along with the filler it has attached to and therefore it fails to be excited. In an unfilled sheet, higher concentration of FWA is achieved because there is less total surface area to dye, hence greater excitation and higher fluorescence.

Chemically crosslinked pulp is more anionic than regular pulp. For a fixed level of FWA, addition of filler actually increases the residual fluorescence compared to a pad doped with the same amount of FWA only. In an unfilled pad, a lower concentration of FWA is achieved because its affinity of FWA to fiber is poor. Given the porous, bulky nature of a pad, most of the FWA leaves with the whitewater when the sheet is formed/pressed. However, when filler is added total affinity (FWA to fiber+FWA to filler) is increased, hence more fluorescent dye remains in the pad. In essence, the filler acts like an inexpensive retention aid for the fluorescent whitening agent.

Filler-only

A 10% PCC loading (Sample 70/1) does little to boost brightness and, in fact, actually has reduced brightness by about 3 points, although one would expect a small gain. Similarly, whiteness has been reduced by 5 points with respect to Control 70.

Blue Dye-only

A 3 ounce/ton addition of blue dye (Sample 70/2) reduces brightness roughly 1 point, but elevates whiteness by 10 points from 86 to 96. Once again, sheet 70/2's whiteness is preferred to Control 70. This simplest of prescriptions produces a very noticeable improvement in whiteness.

Blue Pigment-only Given the poor retention of blue pigment (Samples 70/8, 9, 10, 11), blue dye seems to be the preferred colorant for non-fluorescent tinting of crosslinked pulp. In all cases, visually and spectrally, the addition of blue pigment has little effect in improving whiteness.

FWA-only

A 7 lb/ton addition of FWA (Sample 70/4) boosts brightness by only 1 point instead of the 5 points one would expect with regular pulp. This is due to poor retention as noted earlier. Whiteness is increased from 86 to 103. As expected, at 40 lb/ton FWA, Sample 70/5 shows marginal improvement. Brightness is essentially unchanged and whiteness improves to 107.

Combined

Based on the above, the best prescription appears to be Sample 70/7, which is simply 200 lb/ton PCC and 40 lb/ton FWA. This formulation produces a colored crosslinked pulp that achieves a brightness approaching 82 and a whiteness near 150. Note that for chemically crosslinked pulp, roughly 6 times the amount of FWA is required to achieve the same 5 point gain in brightness one would obtain with regular pulp. A slight optical improvement to the above prescription would be to add a small amount of Blue PTD dye. This would improve the whiteness by about 10 points.

Conclusions

A 3 ounce/ton addition of blue dye reduces brightness 1 point yet elevates whiteness from 86 to 96. This is one of the simplest of all prescriptions yet it produces a considerable improvement in whiteness compared to Control 70.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. Whitened fluff pulp, comprising pulp fibers and a whitening material selected from the group consisting of a white pigment, a colorant, a whitening agent and mixtures thereof.

2. The whitened fluff pulp of claim 1 wherein said white pigment is selected from the group consisting of precipitated calcium carbonate, titanium dioxide, barium sulfate, high brightness chalk and mixtures thereof.

3. The whitened fluff pulp of claim 1 wherein said colorant comprises a blue dye.

4. The whitened fluff pulp of claim 1 wherein said whitening agent comprises a fluorescent whitening agent.

5. The whitened fluff pulp of claim 4 wherein said fluorescent whitening agent is selected from the group consisting of a disulfonated stilbene compound, a tetrasulfonated stilbene compound and a hexasulfonated stilbene compound.

6. The whitened fluff pulp of claim 1 wherein said pulp fibers are selected from the group consisting of unbleached pulp fibers, bleached pulp fibers, superabsorbent fluff pulp fibers, chemically crosslinked fluff pulp fibers and mixtures thereof.

7. The whitened fluff pulp of claim 6 wherein said pulp fibers are selected from the group consisting of chemically crosslinked fluff pulp fibers, citric acid crosslinked fluff pulp fibers and mixtures thereof.

8. The whitened fluff pulp of claim 7 wherein said white pigment is selected from the group consisting of precipitated calcium carbonate, titanium dioxide, barium sulfate, high brightness chalk and mixtures thereof.

9. The whitened fluff pulp of claim 7 wherein said colorant comprises a blue dye.

10. The whitened fluff pulp of claim 7 wherein said whitening agent comprises a fluorescent whitening agent.

11. The whitened fluff pulp of claim 10 wherein said fluorescent whitening agent is selected from the group consisting of a disulfonated stilbene compound, a tetrasulfonated stilbene compound and a hexasulfonated stilbene compound.

12. The method of making a whitened fluff pulp comprising combining pulp fibers with a whitening material, wherein said whitening material is selected from the group consisting of a white pigment, a colorant, a whitening agent and mixtures thereof.

13. The method of claim 12 wherein said white pigment is selected from the group consisting of precipitated calcium carbonate, titanium dioxide, barium sulfate, high brightness chalk and mixtures thereof.

14. The method of claim 12 wherein said colorant comprises a blue dye.

15. The method of claim 12 wherein said whitening agent comprises a fluorescent whitening agent.

16. The method of claim 15 wherein said fluorescent whitening agent is selected from the group consisting of a disulfonated stilbene compound, a tetrasulfonated stilbene compound and a hexasulfonated stilbene compound.

17. The method of claim 12 wherein said pulp fibers are selected from the group consisting of unbleached pulp fibers, bleached pulp fibers, superabsorbent fluff pulp fibers, chemically crosslinked fluff pulp fibers and mixtures thereof.

18. The method of claim 17 wherein said pulp fibers are selected from the group consisting of chemically crosslinked fluff pulp fibers, citric acid crosslinked fluff pulp fibers and mixtures thereof.

19. The method of claim 18 wherein said white pigment is selected from the group consisting of precipitated calcium carbonate, titanium dioxide, barium sulfate, high brightness chalk and mixtures thereof.

20. The method of claim 18 wherein said colorant comprises a blue dye.

21. The method of claim 18 wherein said whitening agent comprises a fluorescent whitening agent.

22. The method of claim 21 wherein said fluorescent whitening agent is selected from the group consisting of a disulfonated stilbene compound, a tetrasulfonated stilbene compound and a hexasulfonated stilbene compound.

* * * * *